United States Patent
Peters

(10) Patent No.: US 9,060,695 B2
(45) Date of Patent: Jun. 23, 2015

(54) SYSTEMS AND METHODS FOR DETERMINING DIFFERENTIAL PULSE TRANSIT TIME FROM THE PHASE DIFFERENCE OF TWO ANALOG PLETHYSMOGRAPHS

(75) Inventor: Daniel J. Peters, Longmont, CO (US)

(73) Assignee: Covidien LP, Mansfield, MA (US)

(*) Notice: Subject to any disclaimer, the term of this patent is extended or adjusted under 35 U.S.C. 154(b) by 795 days.

(21) Appl. No.: 13/307,961

(22) Filed: Nov. 30, 2011

(65) Prior Publication Data
US 2013/0137938 A1    May 30, 2013

(51) Int. Cl.
| A61B 5/0205 | (2006.01) |
| A61B 5/021 | (2006.01) |
| A61B 5/1455 | (2006.01) |
| A61B 5/00 | (2006.01) |
| A61B 5/024 | (2006.01) |

(52) U.S. Cl.
CPC .............. *A61B 5/0205* (2013.01); *A61B 5/0002* (2013.01); *A61B 5/02125* (2013.01); *A61B 5/024* (2013.01); *A61B 5/14552* (2013.01); *A61B 5/7225* (2013.01)

(58) Field of Classification Search
CPC .............. A61B 5/02125; A61B 5/7225; A61B 5/0002; A61B 5/024; A61B 5/0205; A61B 5/14552
USPC ................................................ 600/481–507
See application file for complete search history.

(56) References Cited

U.S. PATENT DOCUMENTS

| 3,835,840 A | 9/1974 | Mount |
| 4,561,447 A | 12/1985 | Kawamura et al. |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |

(Continued)

FOREIGN PATENT DOCUMENTS

| EP | 0443267 | 8/1991 |
| EP | 0755221 | 1/1997 |

(Continued)

OTHER PUBLICATIONS

Addison, Paul S., The Illustrated Wavelet Transform Handbook, Taylor & Francis Group, 2002, pp. 1-353.

(Continued)

*Primary Examiner* — Navin Natnithithadha
*Assistant Examiner* — Eric Messersmith
(74) *Attorney, Agent, or Firm* — Shvarts & Leiz LLP

(57) ABSTRACT

Systems and methods are provided for patient monitors which apply phase detection operations to analog signals to identify differential pulse transit time (DPTT). Photoplethysmograph (PPG) signals measured at two sensor sites may be processed by a phase detection system to identify phase information that allows the calculation of a DPTT. The phase detection system may process analog PPG signals in the analog domain to determine phase information. In some embodiments, the phase detection system may process optical oximetry sensor signals to determine phase information using, for example, interferometric methods.

18 Claims, 14 Drawing Sheets

(56) References Cited

U.S. PATENT DOCUMENTS

| | | |
|---|---|---|
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,353,799 A | 10/1994 | Chance |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,553,614 A | 9/1996 | Chance |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,192,094 B1 | 2/2001 | Hermann et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,397,092 B1 | 5/2002 | Norris et al. |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,708,048 B1 | 3/2004 | Chance |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,957,094 B2 | 10/2005 | Chance et al. |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |

(56) References Cited

U.S. PATENT DOCUMENTS

| | | | |
|---|---|---|---|
| 7,393,327 | B2 | 7/2008 | Inukai |
| 7,400,257 | B2 | 7/2008 | Rivas |
| 7,402,821 | B2 | 7/2008 | Bernhardt |
| 7,455,643 | B1 | 11/2008 | Li et al. |
| 7,481,772 | B2 | 1/2009 | Banet |
| 7,485,095 | B2 | 2/2009 | Shusterman |
| 7,772,997 | B2 | 8/2010 | Frederick et al. |
| 8,047,998 | B2 * | 11/2011 | Kolluri et al. ............... 600/494 |
| 2005/0148885 | A1 | 7/2005 | Tweed et al. |
| 2005/0192488 | A1 | 9/2005 | Bryenton et al. |
| 2005/0251344 | A1 | 11/2005 | Appel et al. |
| 2005/0261594 | A1 | 11/2005 | Banet |
| 2006/0009700 | A1 | 1/2006 | Brumfield et al. |
| 2006/0063992 | A1 | 3/2006 | Yu et al. |
| 2006/0063993 | A1 | 3/2006 | Yu et al. |
| 2006/0079945 | A1 | 4/2006 | Libbus |
| 2006/0206021 | A1 | 9/2006 | Diab |
| 2006/0217614 | A1 | 9/2006 | Takala et al. |
| 2006/0217628 | A1 | 9/2006 | Huiku |
| 2006/0241975 | A1 | 10/2006 | Brown |
| 2006/0285736 | A1 | 12/2006 | Brown |
| 2006/0287603 | A1 | 12/2006 | Bartnik et al. |
| 2007/0066910 | A1 | 3/2007 | Inukai et al. |
| 2007/0083093 | A1 | 4/2007 | Diab |
| 2007/0083097 | A1 | 4/2007 | Fujiwara et al. |
| 2007/0118045 | A1 | 5/2007 | Naghavi et al. |
| 2007/0172392 | A1 | 7/2007 | Sen et al. |
| 2007/0225582 | A1 | 9/2007 | Diab et al. |
| 2007/0249467 | A1 | 10/2007 | Hong et al. |
| 2008/0015451 | A1 | 1/2008 | Hatib et al. |
| 2008/0030468 | A1 | 2/2008 | Ali et al. |
| 2008/0033305 | A1 | 2/2008 | Hatib et al. |
| 2008/0039731 | A1 * | 2/2008 | McCombie et al. .......... 600/485 |
| 2008/0132798 | A1 | 6/2008 | Hong et al. |
| 2008/0214903 | A1 | 9/2008 | Orbach |
| 2008/0214942 | A1 | 9/2008 | Oh et al. |
| 2008/0242955 | A1 | 10/2008 | Uutela et al. |
| 2009/0048497 | A1 | 2/2009 | Keren |
| 2009/0297140 | A1 * | 12/2009 | Heismann et al. ............ 398/16 |
| 2009/0326386 | A1 | 12/2009 | Sethi et al. |
| 2009/0326393 | A1 | 12/2009 | Sethi et al. |
| 2009/0326395 | A1 | 12/2009 | Watson |
| 2010/0081945 | A1 | 4/2010 | Sethi et al. |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. S11-S14.

Fitchett, D., Bouthier, JD, Simon, A. CH., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994, pp. 1-446.

Fung, YC, Biomechanics: Circulation, 2nd Edition, New York, Springer, 1997, pp. 1-571.

Geddes, LA, Handbook of Blood Pressure Measurement, Clifton, New Jersey, Humana Press, 1991, pp. 1-168.

Millasseau, Sandrine C, Guigui, Franck G, Kelly, Ronan P., Prasad, Krishna, Cockcroft, John R., Ritter, James M., Chowienczyk, Philip J., "Noninvasive Assessment of the Digital Volume Pulse: Comparison with the Peripheral Pressure Pulse, Hypertension," vol. 36, No. 6, Dec. 2000, pp. 952-956.

Moyle, John TB, Hahn, CEW, Adams, Anthony P, Pulse Oximetry, Revised Edition, London, BMJ, 1998, pp. 1-140.

Nara, Andrew R., Burns, Michael P., Downs, W. Gregory, Blood Pressure, Redmond, Washington, SpaceLabs, 1989, pp. 1-109.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990, pp. 1-456.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb. 1991, pp. 39-54.

Young, Christopher C., Mark, Jonathan B., White, William, Debree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR DETERMINING DIFFERENTIAL PULSE TRANSIT TIME FROM THE PHASE DIFFERENCE OF TWO ANALOG PLETHYSMOGRAPHS

SUMMARY

Continuous non-invasive blood pressure (CNIBP) monitoring systems allow a patient's blood pressure to be tracked continuously, unlike standard occlusion cuff techniques, and without the hazards of invasive arterial lines. Some CNIBP systems use multiple pulse oximetry type sensors located at multiple body sites on a patient to measure photoplethysmograph (PPG) signals. The resulting multiple PPG signals may be compared against each other to estimate the patient's blood pressure. When the locations of two sensors are at different distances from the heart or along different paths from the heart (e.g., at the finger and forehead), a differential pulse transit time (DPTT) may be determined.

A DPTT may represent the difference in the arrival times of a portion of a cardiac wave between the two locations, and may be determined by comparing corresponding fiducial points in the two PPG signals (e.g., a maximum, minimum, slopes, notches, extrema, any other suitable feature, or any combination thereof). In some embodiments, it may be advantageous to perform phase measurements on analog sensor output signals. This may allow for the reduction of quantization error and error associated with identifying the key features or fiducial points of the waveforms. Performing the measurements in the analog domain may also be faster than calculating the phase difference in software running on a microprocessor.

Systems and methods are provided herein for determining physiological information about a subject with a monitoring device. The monitoring device may receive analog physiological signals from one or more sensors and may use a processor, a phase detector, or both to generate phase information. In some embodiments, the analog physiological signals may include photoplethysmograph signals measured at different body sites of the subject. The monitoring device may calculate DPTT based at least in part on the phase information. The monitoring device may then determine physiological information about the subject based at least in part on the DPTT. In some embodiments, the physiological information may include a blood pressure.

In some embodiments, the systems and methods described herein may be used in CNIBP monitors which may apply analog signal processing operations, optical signal processing operations, digital signal processing operations, any other suitable operations, or any combination thereof to any suitable signals to identify phase information, DPTT, or both.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
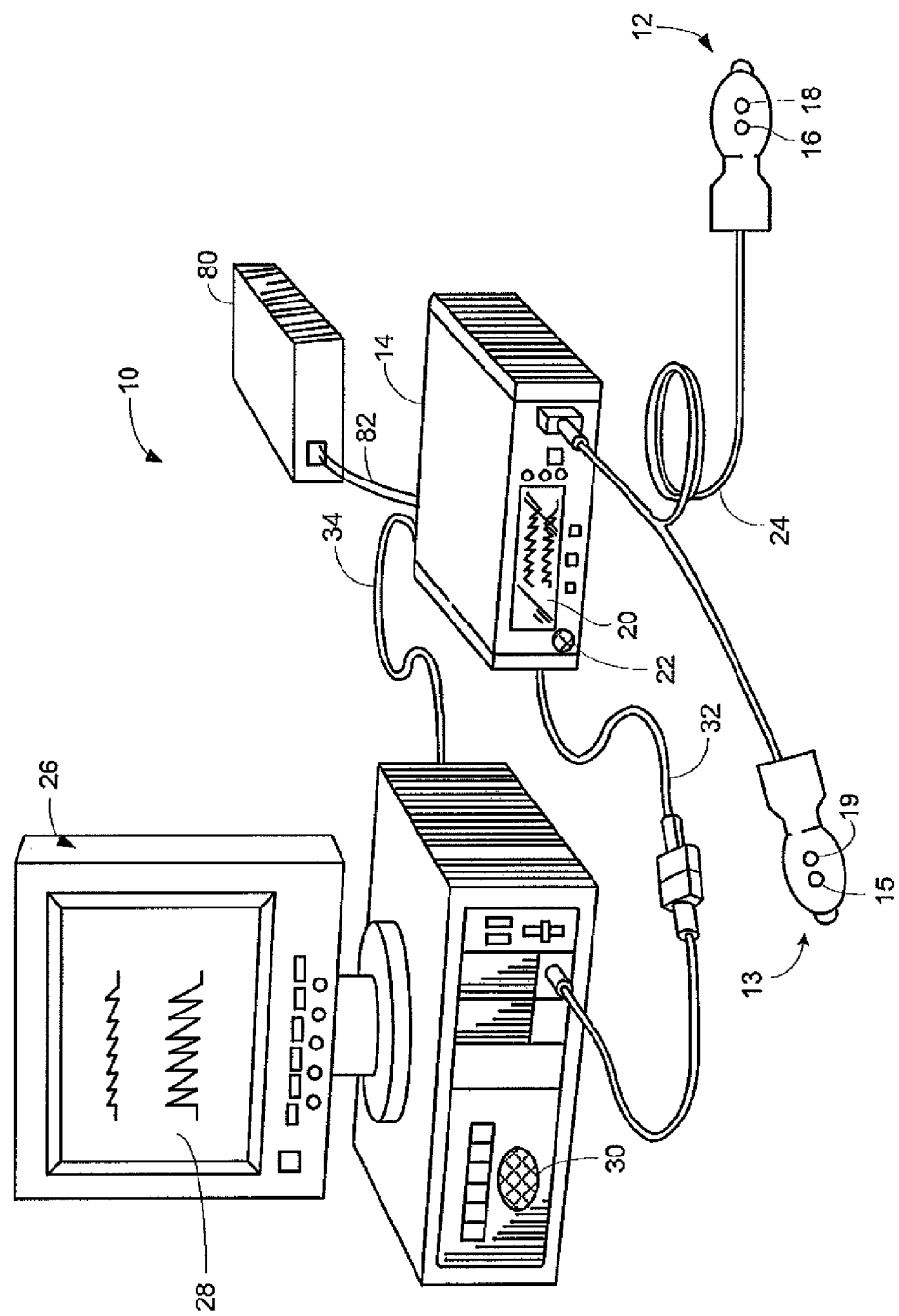
FIG. 1 shows an illustrative patient monitoring system in accordance with an embodiment.

As described above, information about a system, such as the physiological system of human subject, may be determined by applying signal processing techniques to a set of signals. The methods and systems of the present disclosure will be illustrated with reference to the monitoring of an analog physiological signal, which may be a PPG signal. However, it will be understood that the disclosure is not limited to monitoring analog physiological signals and may be usefully applied within a number of signal monitoring contexts.

For illustrative purposes, the systems and techniques disclosed herein may be described in the context of continuous, non-invasive blood pressure monitoring (CNIBP) systems, oximetry systems, and other patient monitoring systems. However, the disclosed systems and methods may be suitable for any signal processing and monitoring application in which phase information may be identified in multiple signals. In particular, the systems and methods described herein have application in any technique that requires the identification of phase information from any periodic signal or any collection of signals.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based at least in part on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_0(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o, \beta_r$=empirically derived absorption coefficients; and
$l(t)$=a combination of concentration and path length from emitter to detector as a function of time.

The traditional approach measures light absorption at two wavelengths (e.g., Red and IR), and then calculates saturation by solving for the "ratio of ratios" as follows:

1. The natural logarithm of Eq. 1 is taken ("log" will be used to represent the natural logarithm) for IR and Red to yield $$\log I = \log I_0 - (s\beta_o + (1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \quad (5)$$

5. Note that, in discrete time, the following approximation may be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 may be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R may be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (11)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R,$$

which defines a cluster of points whose slope of y versus x will give R when $$x=[I(t_2,\lambda_{IR})-I(t_1,\lambda_{IR})]I(t_1,\lambda_R), \quad (12)$$

and $$y=[I(t_2,\lambda_R)-I(t_1,\lambda_R)]I(t_1,\lambda_{IR}). \quad (13)$$

Once R is determined or estimated, for example, using the techniques described above, the blood oxygen saturation may be determined or estimated using any suitable technique for relating a blood oxygen saturation value to R. For example, blood oxygen saturation may be determined from empirical data that may be indexed by values of R, curve fitting, any other suitable methods or interpolative techniques, or any combination thereof.

FIG. 1 is a perspective view of an embodiment of a patient monitoring system 10. System 10 may include sensor unit 12 and monitor 14. In an embodiment, sensor unit 12 may be part of a continuous, non-invasive blood pressure (CNIBP) monitoring system, an oximeter, or both. Sensor unit 12 may include emitter 16 for emitting light at one or more wavelengths into a patient's tissue. A detector 18 may also be provided in sensor 12 for detecting the light originally from emitter 16 that emanates from the patient's tissue after passing through the tissue. Any suitable physical configuration of emitter 16 and detector 18 may be used. In an embodiment, sensor unit 12 may include multiple emitters, detectors, or both, which may be spaced apart. System 10 may also include one or more additional sensor units, such as sensor unit 13, which may take the form of any of the embodiments described herein with reference to sensor unit 12. For example, sensor unit 13 may include emitter 15 and detector 19. Sensor unit 13 may be the same type of sensor unit as sensor unit 12, or sensor unit 13 may be of a different sensor unit type than sensor unit 12. Sensor units 12 and 13 may be capable of being positioned at two different locations on a subject's body. For example, sensor unit 12 may be positioned on a patient's forehead, while sensor unit 13 may be positioned at a patient's fingertip.

Sensor units 12 and 13 may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include a plurality of sensors forming a sensor array in lieu of either or both of sensor units 12 and 13. Each of the sensors of a sensor array may be a complementary metal oxide semiconductor (CMOS) sensor. Alternatively, each sensor of an array may be charged coupled device (CCD) sensor. In an embodiment, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more of sensor units 12 and 13 in accordance with the systems and techniques disclosed herein. It is understood that any number of sensors measuring any number of physiological signals may be used to determine physiological information in accordance with the techniques described herein.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as in a sensor designed to obtain pulse oximetry data from a patient's forehead.

In an embodiment, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., heart rate, blood pressure, blood oxygen saturation) based at least in part on data relating to light emission and detection received from one or more sensor units such as sensor units 12 and 13. In an alternative embodiment, the calculations may be performed on the sensor units or an intermediate device and the result of the calculations may be passed to monitor 14. Further, monitor 14 may include display 20 configured to display the physiological parameters or other information about the system. In the embodiment shown, monitor 14 may also include speaker 22 to provide an audible sound that may be used in various other embodiments, such as for example, sounding an audible alarm in the event that a patient's physiological parameters are not within a predefined normal range. In an embodiment, monitor 14 may include a blood pressure monitor. In alternative embodiments, system 10 may include a stand-alone blood pressure monitor in communication with monitor 14 via a cable or a wireless network link.

In an embodiment, sensor unit 12, sensor unit 13, or both may be communicatively coupled to monitor 14 via a cable 24. However, in other embodiments, a wireless transmission device (not shown) or the like may be used instead of or in addition to cable 24.

In the illustrated embodiment, system 10 includes a multi-parameter patient monitor 26. The monitor 26 may include a cathode ray tube display, a flat panel display (as shown) such as a liquid crystal display (LCD) or a plasma display, or may include any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by monitor 14 (referred to as an "SpO$_2$" measurement), pulse rate information from monitor 14 and blood pressure from monitor 14 on display 28. Multi-parameter patient monitor 26 may include a speaker 30.

Monitor 14 may be communicatively coupled to multi-parameter patient monitor 26 via a cable 32 or 34 that is coupled to a sensor input port or a digital communications port, respectively. In some embodiments, Monitor 14 may communicate wirelessly with multi-parameter patient monitor 26 (not shown). In addition, monitor 14, multi-parameter patient monitor 26, or both may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable signal calibration device. Calibration device 80 may be communicatively coupled to monitor 14 via cable 82, may communicate wirelessly (not shown), or both. In other embodiments, calibration device 80 may be completely integrated within monitor 14. For example, calibration device 80 may take the form of any invasive or non-invasive blood pressure monitoring or measuring system used to generate reference blood pressure measurements for use in calibrating a CNIBP monitoring technique as described herein. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference signal measurements obtained from some other source (e.g., an external invasive or non-invasive physiological measurement system).

Calibration device 80 may also access reference signal measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle or a different periodic cycle. Reference blood pressure measurements may be generated when recalibration is triggered.

Figure 2:
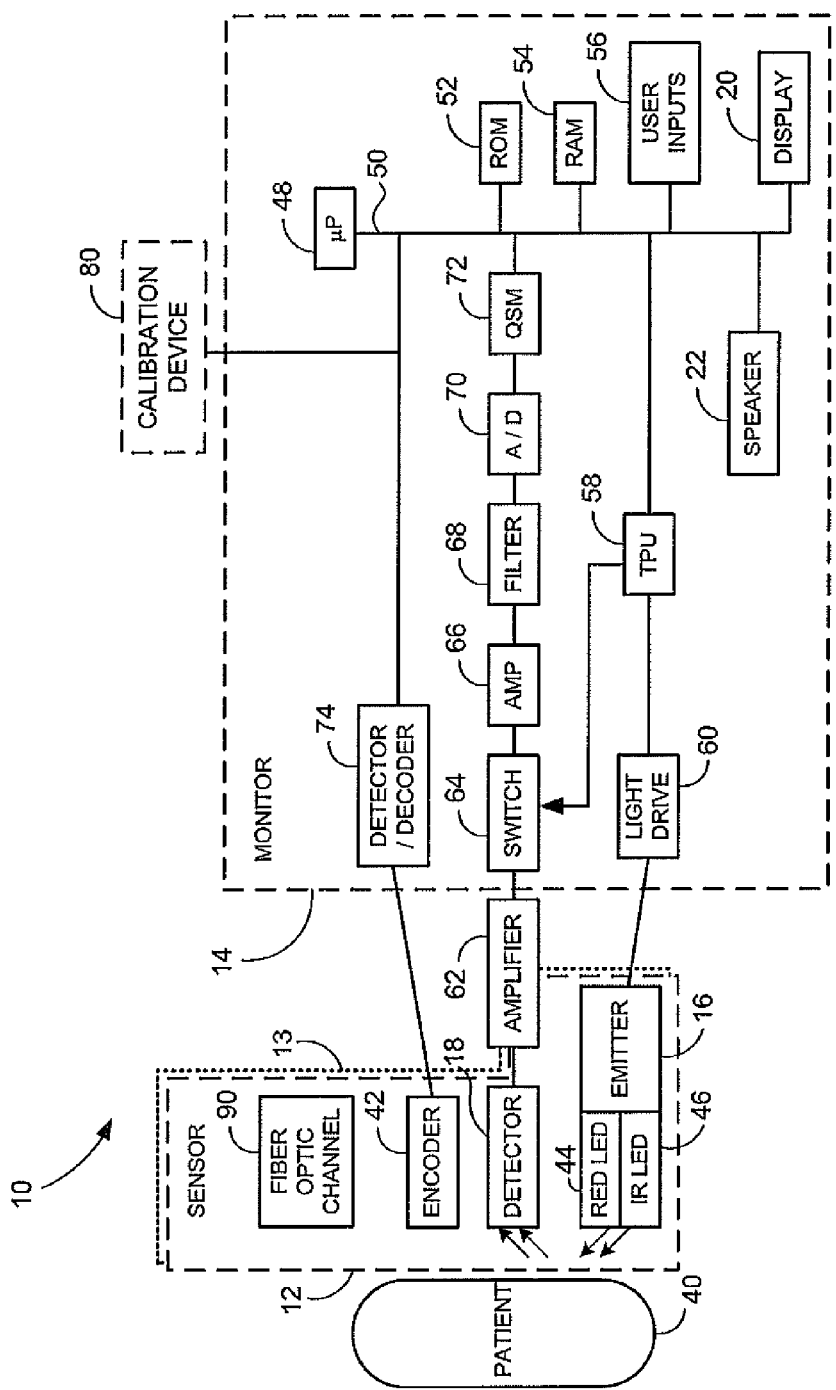
FIG. 2 is a block diagram of the illustrative patient monitoring system of FIG. 1 coupled to a patient in accordance with an embodiment.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2, Because sensor units 12 and 13 may include similar components and functionality, only sensor unit 12 will be discussed in detail for ease of illustration. It will be understood that any of the concepts, components, and operation discussed in connection with sensor unit 12 may be applied to sensor unit 13 as well (e.g., emitter 16 and detector 18 of sensor unit 12 may be similar to emitter 15 and detector 19 of sensor unit 13). It will be noted that patient monitoring system 10 may include one or more additional sensor units or probes, which may take the form of any of the embodiments described herein with reference to sensor units 12 and 13 (FIG. 1). These additional sensor units included in system 10 may take the same form as sensor unit 12, or may take a different form. In an embodiment, multiple sensors (distributed in one or more sensor units) may be located at multiple different body sites on a patient.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In one embodiment, the Red wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a Red light while a second emits only an IR light. In another example, the wavelengths of light used are selected based at least in part on the specific location of the sensor.

It will be understood that, as used herein, the term "light" may refer to energy produced by radiation sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of emitter 16.

In an embodiment, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance, reflectance, or both of light in tissue 40. That is, when more light at a certain wavelength is absorbed or reflected, less light of that wavelength is received from the tissue by detector 18. After converting the received light to an electrical signal, detector 18 may send the signal to monitor 14, where physiological parameters may be calculated based at least in part on the absorption of the Red and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables, calibration coefficients, or any combination thereof stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which, for example, blood pressure and other measurements may be determined based at least in part on the signal or signals received at sensor unit 12. For example, some pulse oximetry sensors rely on equations to relate an area under a pulse of a photoplethysmograph (PPG) signal to determine blood pressure. These equations may contain coefficients that depend at least in part on a patient's physiological characteristics as stored in encoder 42. Encoder 42 may, for instance, be a coded resistor which stores values corresponding to the type of sensor unit 12 or the type of each sensor in the sensor array, the wavelengths of light emitted by emitter 16 on each sensor of the sensor array, the patient's characteristics, any other suitable information, or any combination thereof. In another embodiment, encoder 42 may include a memory on which one or more of the following information may be stored for communication to monitor 14: the type of sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, sensor unit 12 may include any suitable components to receive optical oximetry sensor signals, transmit optical oximetry sensor signals, or both. For example, sensor unit 12 may include fiber optic channel 90. Fiber optic channel 90 may receive optical signals from Red LED 44, IR LED 46, any other suitable light source, or any combination thereof. Fiber optic channel 90 may be coupled to one or more optical fibers, optical amplifiers, waveguides, optical multiplexers, lenses, mirrors, photodetectors, fiber optic sensors, any other suitable components, or any combination thereof through any suitable communications path or connection.

In an embodiment, signals from sensor unit 12 (e.g., detector 18, encoder 42, fiber optic channel 90) may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be read-only memory (ROM) 52, random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that may be interpreted by microprocessor 48. This information may be data or may take the form of computer-executable instructions, such as software applications, that cause the microprocessor to perform certain functions, computer-implemented methods, or both. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store the desired information and which may be accessed by components of the system.

In the embodiment shown, time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 fills up. In one embodiment, there may be multiple separate parallel paths having components equivalent to amplifier 66, filter 68, A/D converter 70, any other suitable component, or any combination thereof for multiple light wavelengths or spectra received.

In an embodiment, microprocessor 48 may determine the patient's physiological parameters, such as $SpO_2$, pulse rate, blood pressure, any other suitable parameter, or any combination thereof using various algorithms, look-up tables, or both based at least in part on the value of the received signals, data corresponding to the light received by detector 18, or both. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue may be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, may be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) may degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals or otherwise identify noise components in order to prevent them from affecting measurements of physiological parameters derived from the sensor signals.

Pulse oximeters, in addition to providing other information, may be utilized for continuous non-invasive blood pressure monitoring. As described in Chen et al., U.S. Pat. No. 6,599,251, the entirety of which is incorporated herein by reference, PPG and other pulse signals obtained from multiple probes may be processed to calculate the blood pressure of a patient. In particular, blood pressure measurements may be derived based at least in part on a comparison of time differences between certain components of the pulse signals detected at each of the respective probes. As described in U.S. patent application Ser. No. 12/242,238, filed on Sep. 30, 2008 and entitled "Systems and Methods For Non-Invasive Blood Pressure Monitoring," the entirety of which is incorporated herein by reference, blood pressure may also be derived by processing time delays detected within a single PPG or pulse signal obtained from a single pulse oximeter probe. In addition, as described in U.S. patent application Ser. No. 12/242,867, filed on Sep. 30, 2008 and entitled "Systems and Methods For Non-Invasive Continuous Blood Pressure Determination," the entirety of which is incorporated herein by reference, blood pressure may also be obtained by calculating the area under certain portions of a pulse signal. Finally, as described in U.S. patent application Ser. No. 12/242,862, filed on Sep. 30, 2008 and entitled "Systems and Methods For Maintaining Blood Pressure Monitor Calibration," the entirety of which is incorporated herein by reference, a blood pressure monitoring device may be recalibrated in response to arterial compliance changes.

As described above, some CNIBP monitoring techniques utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p = a + b \cdot \ln(T) \quad (14)$$

where a and b are constants that may be dependent upon the nature of the subject and the nature of the signal detecting devices. Other suitable equations using an elapsed time between corresponding points of a pulse signal may also be used to derive an estimated blood pressure measurement.

In an embodiment, Eq. 14 may include a non-linear function which is monotonically decreasing and concave upward in T in a manner specified by the constant parameters (in addition to or instead of the expression of Eq. 14). Eq. 14 may be used to calculate an estimated blood pressure from the time difference T between corresponding points of a pulse signal received by two sensors or probes attached to two different locations of a subject.

In an embodiment, constants a and b in Eq. 14 above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

In an embodiment, the calibration may include performing calculations mathematically equivalent to $$a = c_1 + \frac{c_2(P_0 - c_1)}{\ln(T_0) + c_2} \quad (15)$$

and $$b = \frac{P_0 - c_1}{\ln(T_0) + c_2} \quad (16)$$

to obtain values for the constants a and b, where $c_1$ and $c_2$ are parameters that may be determined, for example, based at least in part on empirical data.

In an embodiment, the calibration may include performing calculations mathematically equivalent to $$a = P_0 - (c_3 T_0 + c_4) \ln(T_0) \quad (17)$$

and $$b = c_3 T_0 + c_4 \quad (18)$$

where a and b are first and second parameters and $c_3$ and $c_4$ are parameters that may be determined, for example, based at least in part on empirical data.

Parameters $c_1$, $c_2$, $c_3$, and $c_4$ may be predetermined constants empirically derived using experimental data from a number of different patients. A single reference blood pressure reading from a patient, including reference blood pressure $P_0$ and elapsed time $T_0$ from one or more signals corresponding to that reference blood pressure, may be combined with such inter-patient data to calculate the blood pressure of a patient. The values of $P_0$ and $T_0$ may be referred to herein as a calibration point. According to this example, a single calibration point may be used with the predetermined constant parameters to determine values of constants a and b for the patient (e.g., using Eqs. 15 and 16 or 17 and 18). The patient's blood pressure may then be calculated using Eq. 14. Recalibration may be performed by collecting a new calibration point and recalculating the constants a and b used in Eq. 14. Calibration and recalibration may be performed using calibration device 80 (FIG. 1).

In an embodiment, multiple calibration points from a patient may be used to determine the relationship between the patient's blood pressure and one or more PPG signals. This relationship may be linear or non-linear and may be extrapolated, interpolated, or both to define the relationship over the range of the collected recalibration data. For example, the multiple calibration points may be used to determine values for parameters $c_1$ and $c_2$ or $c_3$ and $c_4$ (described above). These determined values may be based at least in part on information about the patient (intra-patient data) instead of information that came from multiple patients (inter-patient data). As another example, the multiple calibration points may be used to determine values for parameters a and b (described above). Instead of calculating values of parameters a and b using a single calibration point and predetermined constants, values for parameters a and b may be empirically derived from the values of the multiple calibration points. As yet another example, the multiple calibration points may be used directly to determine the relationship between blood pressure and PPG signals. Instead of using a predefined relationship (e.g., the relationship defined by Eq. 14), a relationship may be directly determined from the calibration points.

Additional examples of continuous and non-invasive blood pressure monitoring techniques are described in Chen et al., U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

Figure 3:
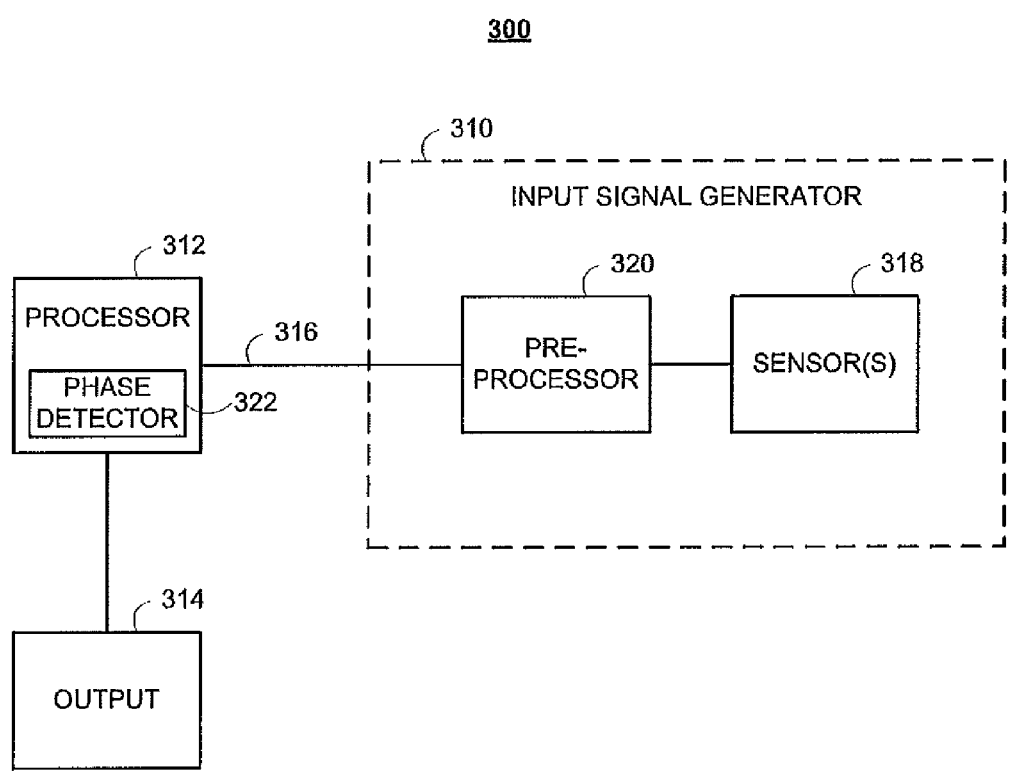
FIG. 3 is a block diagram of an illustrative signal processing system in accordance with an embodiment.

FIG. 3 is an illustrative signal processing system 300 in accordance with an embodiment that may implement the non-invasive blood pressure techniques described herein. In this embodiment, input signal generator 310 generates an input signal 316. As illustrated, input signal generator 310 may include pre-processor 320 coupled to one or more sensors 318, which may provide one or more input signals 316. In an embodiment, pre-processor 320 may be an oximeter and input signal 316 may be a PPG signal. In an embodiment, pre-processor 320 may be any suitable signal processing device and input signal 316 may include one or more PPG signals and one or more other physiological signals, such as an electrocardiogram (ECG) signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a pre-determined set of processing operations to the signal provided by sensor 318 to produce input signal 316 that may be appropriately interpreted by processor 312, phase detection system 322, or both. Pre-processor 320 may also perform any of the following operations on the signal provided by sensor 318: analog-to-digital conversion, reshaping the signal for transmission, multiplexing the signal, modulating the signal onto carrier signals, compressing the signal, encoding the signal, filtering the signal, convolving the signal with a reference signal, any other suitable operation, or any combination thereof.

In an embodiment, signal 316 may include PPG signals at one or more frequencies, such as a Red PPG signal and an IR PPG signal. In an embodiment, signal 316 may include signals measured at one or more sites on a patient's body, for example, a patient's finger, toe, ear, arm, or any other body site. In an embodiment, signal 316 may include multiple types of signals (e.g., one or more of an ECG signal, an EEG signal, an acoustic signal, an optical signal, a signal representing a blood pressure, and a signal representing a heart rate). Signal 316 may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, or any combination thereof.

In an embodiment, signal 316 may be coupled to processor 312, phase detection system 322, or both. Processor 312 may be any suitable software, firmware, hardware, or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, be configured of analog electronic components. Processor 312 may perform the calculations associated with the information determination techniques of the present disclosure as well as the calculations associated with any calibration of processing system 300 or other auxiliary functions. For example, processor 312 may locate one or more fiducial points in one or more signals, determine one or more DPTTs, and compute one or more of a systolic blood pressure, a diastolic blood pressure, and a mean arterial pressure. Processor 312 may perform any suitable signal processing of signal 316 to filter signal 316, such as any suitable band-pass filtering, adaptive filtering, closed-loop filtering, any other suitable filtering, or any combination thereof. Processor 312 may also receive input signals from additional sources (not shown). For example, processor 312 may receive an input signal containing information about treatments provided to the patient. Additional input signals may be used by processor 312 in any of the calculations or operations it performs in accordance with processing system 300.

Processor 312 may be coupled to one or more phase detection systems, such as phase detection system 322, any other suitable phase detector or phase detection system, or any combination thereof. Phase detection system 322 may include any suitable software, hardware, or both for determining phase information from signal 316, two or more sensor signals, any other suitable signal, or any combination thereof. In some embodiments, phase detection system 322 may include any suitable circuitry such as one or more analog phase detection systems, optical phase detection systems, digital signal processors, programmable logic devices, any other suitable devices, or any combination thereof.

In some embodiments, phase detection system 322 may perform phase measurements in the analog domain. For example, phase detection system 322 may include an analog phase detection system, such as a logarithmic amplifier based phase detection system, an exclusive-OR (XOR) based phase detection system, a flip-flop based phase detection system, a mixer based phase detection system, any other suitable phase detector or phase detection systems, or any combination thereof.

In some embodiments, phase detection system 322 may perform phase measurements optically. For example, phase detection system 322 may include an interferometer that analyzes optical sensor output signals received via, for example, fiber-optic cables. The phase information may be used by processor 312 to, for example, determine differential pulse transit time information, any other suitable information, or any combination thereof.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to blood pressure monitoring, including current blood pressure calibration values, blood pressure monitoring calibration thresholds, and patient blood pressure history. In an embodiment, processor 312 may store physiological measurements or previously received data from signal 316 in a memory device for later retrieval. In an embodiment, processor 312 may store calculated values, such as a systolic blood pressure, a diastolic blood pressure, a blood oxygen saturation, a differential pulse transit time, a fiducial point location or characteristic, or any other calculated values, in a memory device for later retrieval.

Processor 312 may be coupled to a calibration device. This coupling may take any of the forms described above with reference to calibration device 80 within system 10. For example, the calibration device may be a stand-alone device that may be in wireless communication with processor 312, or may be completely integrated with processor 312.

Processor 312 may be coupled to a calibration device that may generate, or receive as input, reference measurements for use in calibration calculations. This coupling may occur through a recalibration signal transmitted via a wired or wireless communications path. In an embodiment, processor 312 is capable of transmitting a command to calibration device 80 to initiate a recalibration procedure.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor units 12 and 13 (FIGS. 1 and 2) and monitor 14 (FIGS. 1 and 2) and processor 312, phase detection system 322, or both may be implemented as part of monitor 14 (FIGS. 1 and 2). In some embodiments, portions of system 300 may be configured to be portable. For example, all or part of system 300 may be embedded in a small, compact object carried with or attached to the patient (e.g., a watch, other piece of jewelry, or a cellular telephone). In such embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In such embodiments, a wireless transceiver (not shown) may also be included in system 300 to enable wireless communication with other components of system 10. For example, pre-processor 320 may output signal 316 over BLUETOOTH, 802.11, WiFi, WiMAX, cable, satellite, infrared, or any other suitable transmission scheme. BLUETOOTH is a certification mark owned by BLUETOOTH SIG, INC. WIMAX is a certification mark owned by WiMAX Forum CORPORATION. In an embodiment, a wireless transmission scheme may be used between any communicating components of system 300.

Pre-processor 320 or processor 312 may determine the locations of pulses within a periodic signal 316 (e.g., a PPG signal) using a pulse detection technique. For ease of illustration, the following pulse detection techniques will be described as performed by processor 312, phase detection system 322, or both, but any suitable processing device (e.g., pre-processor 320) may be used to implement any of the techniques described herein.

Figure 4:
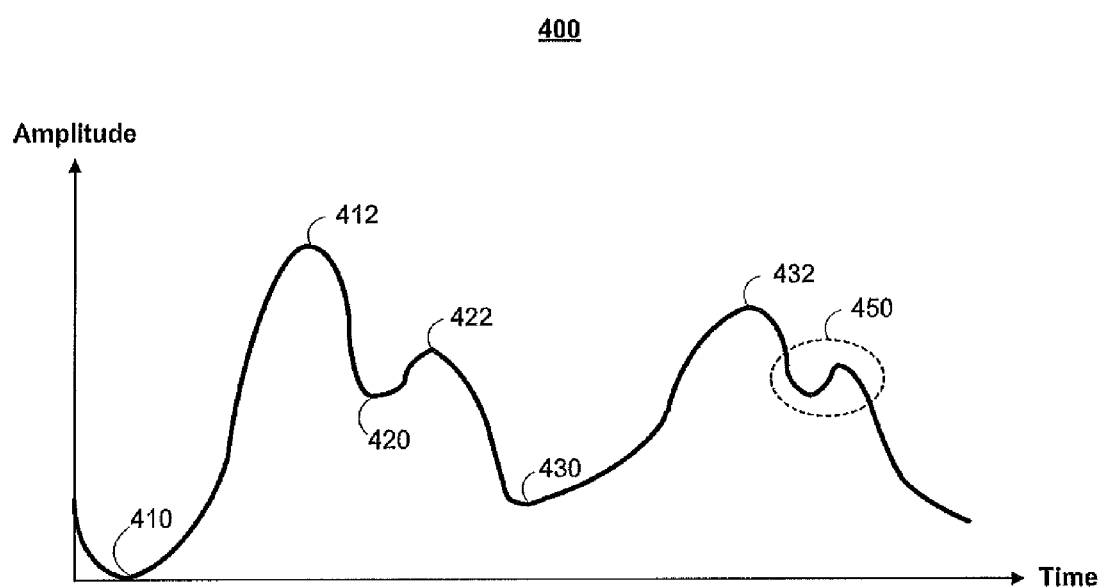
FIG. 4 is an illustrative signal which may be analyzed in accordance with an embodiment.

An illustrative PPG signal 400 is depicted in FIG. 4. Processor 312 may receive PPG signal 400, and may identify local minimum point 410, local maximum point 412, local minimum point 420, and local maximum point 422 in the PPG signal 400. Processor 312 may pair each local minimum point with an adjacent maximum point. For example, processor 312 may pair points 410 and 412 to identify one segment, points 412 and 420 to identify a second segment, points 420 and 422 to identify a third segment and points 422 and 430 to identify a fourth segment. The slope of each segment may be measured to determine whether the segment corresponds to an upstroke portion of the pulse (e.g., a positive slope) or a downstroke portion of the pulse (e.g., a negative slope) portion of the pulse. A pulse may be defined as a combination of at least one upstroke and one downstroke. For example, the segment identified by points 410 and 412 and the segment identified by points 412 and 420 may define a pulse.

According to an embodiment, PPG signal 400 may include a dichrotic notch 450 or other notches (not shown) in different sections of the pulse (e.g., at the beginning (referred to as an ankle notch), in the middle (referred to as a dichrotic notch), or near the top (referred to as a shoulder notch)). Processor 312 may identify notches and either utilize or ignore them when detecting the pulse locations. In some embodiments, processor 312 may compute the second derivative of the PPG signal to find the local minima and maxima points and may use this information to determine a location of, for example, a dichrotic notch. Additionally, processor 312 may interpolate between points in signal 316 or between points in a processed signal using any interpolation technique (e.g., zero-order hold, linear interpolation, higher-order interpolation techniques). Some pulse detection techniques that may be performed by processor 312 are described in more detail in co-pending, commonly assigned U.S. patent application Ser. No. 12/242,908, filed Sep. 30, 2008 and entitled "SYSTEMS AND METHODS FOR DETECTING PULSES IN A PPG SIGNAL," which is incorporated by reference herein in its entirety.

Figure 5:
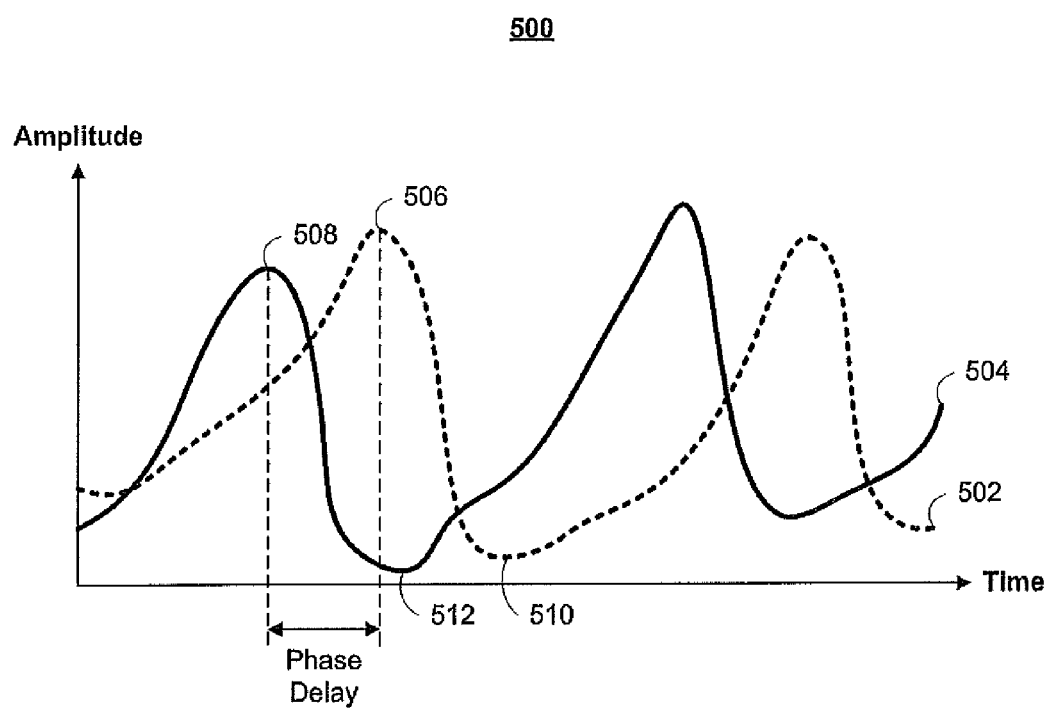
FIG. 5 is a plot that illustrates a phase delay between two signals in accordance with an embodiment.

FIG. 5 illustrates a phase delay between two signals in accordance with the systems and methods described herein. In some embodiments, plot 500 may include photoplethysmograph (PPG) signals generated by reflectance probes positioned on a subject's forehead for approximately ten seconds. For example, plot 500 may include signal 502 received from a first sensor and signal 504 received from a second sensor. Though the location of the troughs of this signal (e.g., troughs 510 and 512) may be more easily distinguished than the peaks (e.g., peaks 506 and 508), neither peaks nor troughs are particularly distinct.

In some embodiments, processor 312 may receive signals 502 and 504, and may identify local maximum points 506 and 508, respectively, and local minimum points 510 and 512, respectively. A received signal may be generated by sensor unit 12, sensor unit 13, or both (FIG. 1), which may each include any of the physiological sensors described herein, or any other sensor. A received signal may be signal 316, which may be generated by a pre-processor 320 coupled between processor 312 and sensor 318 (FIG. 3). In some embodiments, a received signal may include multiple signals in the form of a multi-dimensional vector signal, a frequency- or time-multiplexed signal, any other suitable form, or any combination thereof. For example, the signals may include two or more PPG signals, which may be measured at two or more respective different body sites of a subject.

Processor 312 may analyze each signal to identify segments, pulses, or both in accordance with some embodiments of the present disclosure. In some embodiments, signals 502, 504, any other suitable signal, or any combination thereof may be filtered and processed to sharpen the extrema of the signals, provide more accurate fiducial points to use in physiological parameter calculations, or both.

In an embodiment, as discussed above, two different fiducial points, identified in signals measured at two different body sites of a subject, may allow a differential pulse transit time (DPTT) to be calculated, which may then be used to determine, for example, the subject's blood pressure. For example, signals 502, 504, any other suitable signal, or any combination thereof may be provided in digital form using, for example, an analog to digital converter and a phase measurement may be performed by, for example, subtracting the times associated with each signal's maximum and minimum points to calculate a phase delay. Thus, differential pulse transit time may be measured by digitizing each sensor's analog signal and subtracting the times of key features of the waveforms, such as local minimums (e.g., troughs 510 and 512), and maximums (e.g., peaks 506 and 508).

The present disclosure relates to systems and methods for providing more direct ways of measuring the phase difference by transmitting two sensor signals to a phase detection system in analog form, optical form, or both. It will be understood that different techniques may be used for measuring phase difference, such as the techniques described below with reference to FIGS. 6-13. In some embodiments, a single technique may be used to measure phase difference. For example, a technique with the lowest probability of measurement error for a given set of operating conditions may be used to measure phase difference. In some embodiments, multiple techniques may be used to measure phase difference. For example, the phase difference may be determined by averaging the phase differences measured using two or more techniques. In another example, the phase difference may be determined by selecting the most accurate phase difference with the lowest probability of error from among the phase differences measured using two or more techniques.

Figure 6:
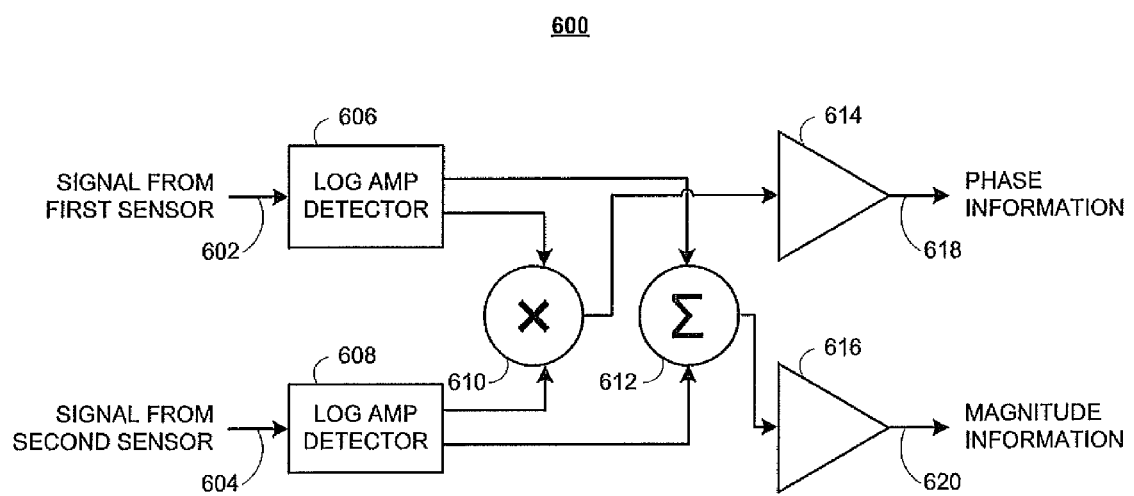
FIG. 6 is a block diagram of an illustrative logarithmic amplifier based phase detection system in accordance with an embodiment.

FIG. 6 is a block diagram of an illustrative logarithmic amplifier based phase detection system 600 in accordance with some embodiments of the present disclosure. In some embodiments, phase detection system 600 may be an illustrative implementation of phase detection system 322 (FIG. 3). For example, phase detection system 600 may provide phase information to processor 312 to determine differential pulse transit time information, any other suitable information, or any combination thereof. In some embodiments, phase detection system 600 may be implemented either partially or wholly using an integrated circuit or microprocessor, such as an Analog Devices AD8302 gain and phase detector. ANALOG DEVICES is a registered trademark owned by Analog Devices, Inc.

Phase detection system 600 may include any suitable software, hardware, or both for determining phase information from two or more analog signals, such as signals 602 (e.g., "signal from first sensor") and 604 (e.g., "signal from second sensor"). For example, signals 602 and 604 may be generated by sensor unit 12 and sensor unit 13, respectively (FIG. 1), which may each include any of the physiological sensors described herein, or any other sensor. In another example, signals 602 and 604 may be generated from signal 316, which may be generated by pre-processor 320 coupled between processor 312 and sensor 318 (FIG. 3). In some embodiments, signals 602 and 604 may be generated from a multi-dimensional vector signal, a frequency- or time-multiplexed signal, any other suitable signal, or any combination thereof. For example, signals 602 and 604 may be PPG signals, which may be measured at two or more respective different body sites of a subject. In another example, signals 602 and 604 may be PPG signals convolved with a sinusoid to allow for ease of analysis by phase detection system 600 because phase detection system 600 may be, for example, more suited to receive a specific waveform such as a sinusoid.

Phase detection system 600 may include any suitable components for performing phase measurements in the analog domain, such as one or more of the following components: logarithmic amplifiers (log amps) 606 and 608, phase detector 610, adder 612, output amplifiers 614 and 616, any other any other suitable component or circuitry, or any combination thereof. In some embodiments, log amps 606 and 608 and phase detector 610 may process signals 602 and 604 and deliver gain and phase information to output amplifiers 614 and 616, which may determine final gain and phase scaling.

Log amps 606 and 608 may receive signals 602 and 604, respectively, and provide output signals to phase detector 610, adder 612, any other suitable component, or any combination thereof. Log amps 606 and 608 may be, for example, identical logarithmic amplifiers in monolithic form and may each include a cascade of linear, limiting, or both gain stages with demodulating detectors.

Phase detector 610 may be, for example, an exclusive-OR (XOR) style digital phase detector, a multiplier style phase detector, a mixer style phase detector, any other suitable phase detector, or any combination thereof. In some embodiments, phase detector 610 may use fully differential signaling to maintain balanced delays along both received signal paths. In some embodiments, phase detector 610 may analyze the phase difference in the output of log amps 606 and 608 and provide an output signal corresponding to the phase difference to amplifier 614, which may provide phase information in the form of signal 618. Signal 618 may be any suitable signal for providing phase information, such as an analog signal (e.g., voltage, current), digital signal, optical signal, multiplexed signal, multi-dimensional vector signal, any other suitable signal, or any combination thereof. For example, signal 618 may be a voltage signal which represents the difference in phase between signals 602 and 604.

Adder 612 may be, for example, any suitable component for determining the difference, ratio, or both of two signals. In some embodiments, adder 612 may analyze the difference in the output of log amps 606 and 608 and provide an output signal corresponding to the magnitude of the signal level difference to amplifier 616, which may provide magnitude or gain information in the form of signal 620. Signal 620 may be any suitable signal for providing magnitude or gain information, such as an analog signal (e.g., voltage, current), digital signal, optical signal, multiplexed signal, multi-dimensional vector signal, any other suitable signal, or any combination thereof. For example, signal 620 may be a voltage signal which represents the difference in magnitude between signals 602 and 604.

Figure 7:
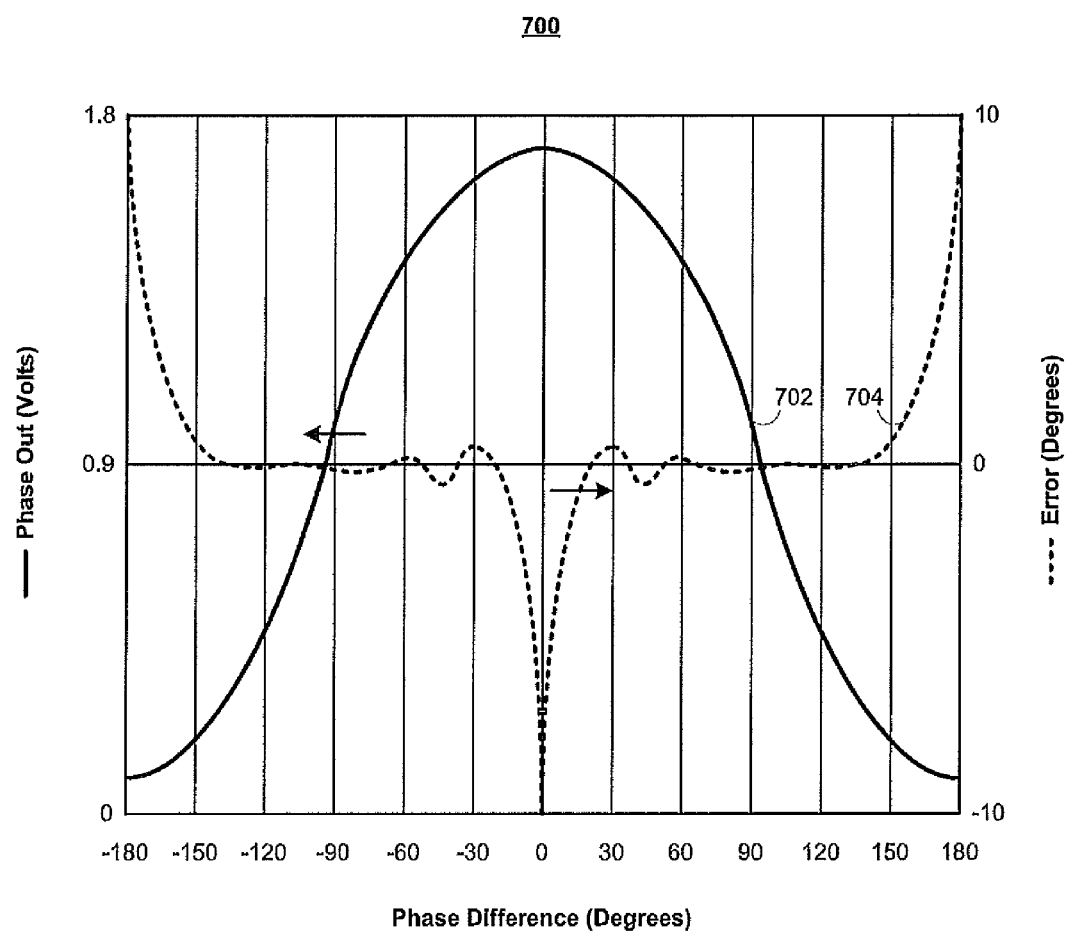
FIG. 7 shows illustrative signal output data from the phase detection system shown in FIG. 6 in accordance with an embodiment.

FIG. 7 shows illustrative signal output data 700 from the phase detection system 600 (FIG. 6) in accordance with some embodiments of the present disclosure. An illustrative voltage plot 702 (e.g., "Phase Out") is shown for the output voltage of signal 618 as a function of the phase difference between signals 602 and 604. An illustrative error plot 704 (e.g., "Error") is shown for the output voltage of signal 618 as a function of the phase difference between signals 602 and 604. As shown in error plot 704, the measurement error may increase as the phase difference between signals 602 and 604 increases. In some embodiments, a known phase shift may be added to signal 602, 604, or both to adjust the phase difference between signals 602 and 604 to a region where the error is relatively low (e.g., between 60 and 120 degrees). The phase shift may then be subtracted from the output of phase detector 610.

Figure 8:
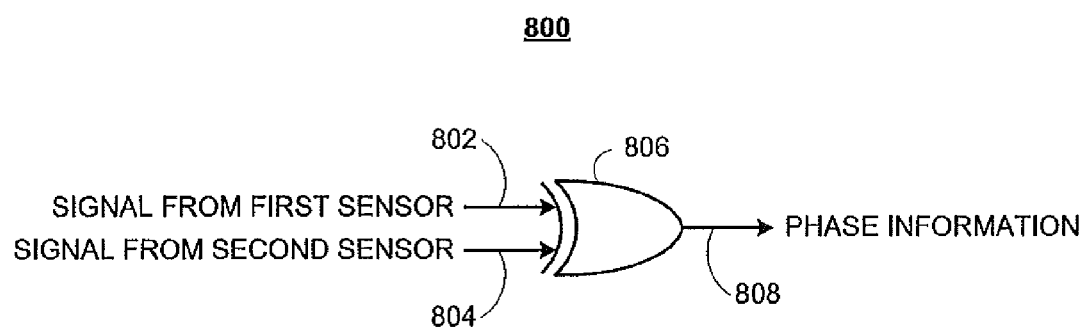
FIG. 8 is a block diagram of an illustrative exclusive-OR based phase detection system in accordance with an embodiment.

FIG. 8 is a block diagram of an illustrative exclusive-OR (XOR) logic gate based phase detection system 800 in accordance with some embodiments of the present disclosure. In some embodiments, phase detection system 800 may be an illustrative implementation of phase detection system 322 (FIG. 3). For example, phase detection system 800 may provide phase information to processor 312 to determine differential pulse transit time information, any other suitable information, or any combination thereof.

Phase detection system 800 may include any suitable software, hardware, or both for determining phase information from two or more analog signals, such as signals 802 (e.g., "signal from first sensor") and 804 (e.g., "signal from second sensor"). For example, signals 802 and 804 may be generated by sensor unit 12 and sensor unit 13, respectively (FIG. 1), which may each include any of the physiological sensors described herein, or any other sensor. In another example, signals 802 and 804 may be generated from signal 316, which may be generated by pre-processor 320 coupled between processor 312 and sensor 318 (FIG. 3). In some embodiments, signals 802 and 804 may be generated from a multi-dimensional vector signal, a frequency- or time-multiplexed signal, any other suitable signal, or any combination thereof. For example, signals 802 and 804 may be PPG signals, which may be measured at two or more respective different body sites of a subject. In another example, signals 802 and 804 may be PPG signals convolved with a square wave to allow for ease of analysis by phase detection system 800 because phase detection system 800 may be, for example, more suited to receive a specific waveform such as a square wave. In another example, signals 802 and 804 may be PPG signals filtered by a high pass filter, such as a derivative filter, and inverted and may be processed using a threshold to convert, for example, peaks to a digital 1.

Phase detection system 800 may include any suitable components for performing phase measurements in the analog domain, such as XOR logic gate 806, any other any other suitable component or circuitry, or any combination thereof. In some embodiments, XOR logic gate 806 may process signals 802 and 804 and output phase information via signal 808. For example, XOR logic gate 806 may analyze the difference in signals 802 and 804 and provide an output signal corresponding to the phase difference in the form of signal 808. In some embodiments, signal 808 may be applied to a low-pass filter to provide an analog voltage proportional to the phase difference between signals 802 and 804.

Signal 808 may be any suitable signal for providing phase information, such as an analog signal (e.g., voltage, current), digital signal, optical signal, multiplexed signal, multi-dimensional vector signal, any other suitable signal, or any combination thereof. For example, signal 808 may be a voltage signal which represents the difference in phase between signals 802 and 804.

Figure 9:
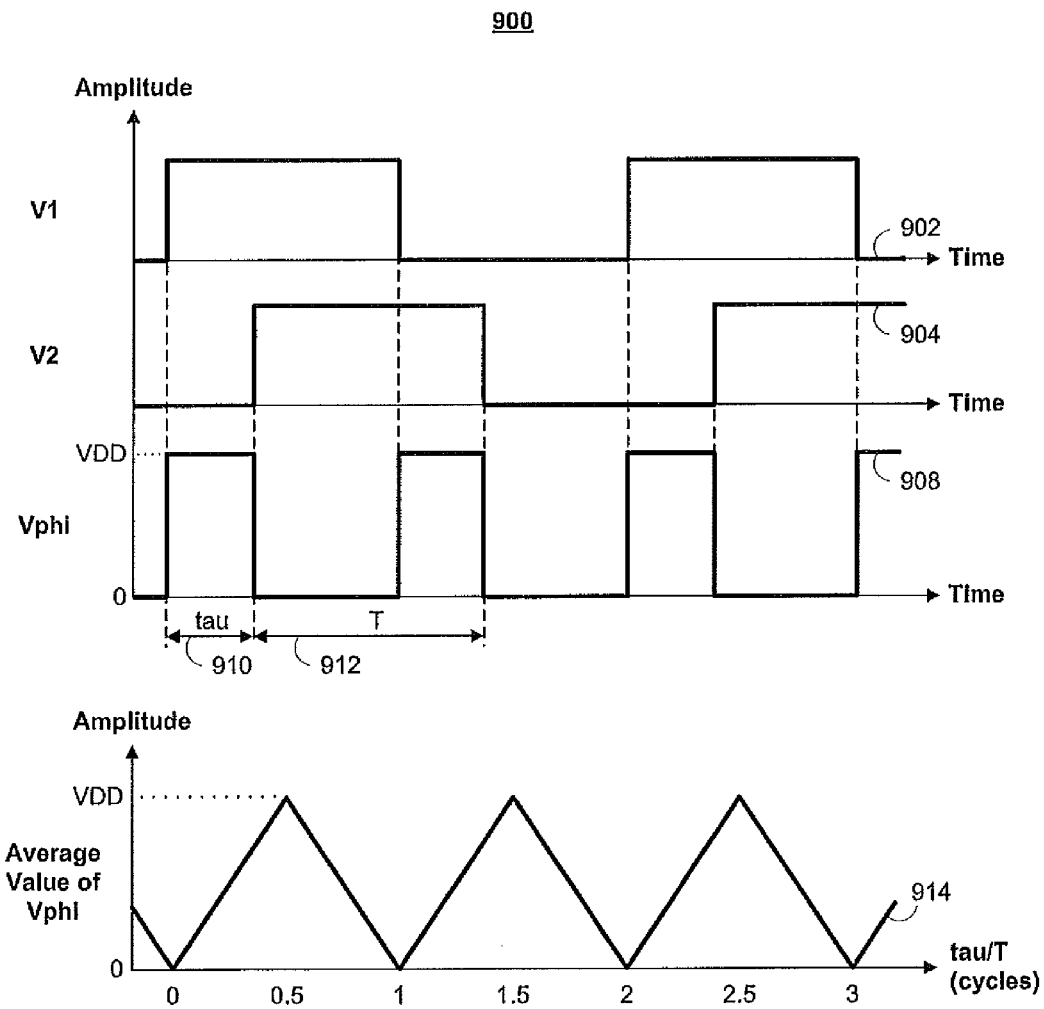
FIG. 9 shows illustrative signal plots for the phase detection system of FIG. 8 in accordance with an embodiment.

FIG. 9 shows illustrative amplitude-time signal plots 900 for phase detection system 800 (FIG. 8) in accordance with some embodiments of the present disclosure. Signal plots 902, 904, and 908 are representative of signals 802, 804, and 808, respectively. In an example, phase detection system 800 may provide signal 908 with logic low output (e.g., Vphi=0) when signals 902 and 904 are at substantially the same level (e.g., both high or both low) and logic high output (e.g., Vphi=VDD) when signals 902 and 904 are at substantially different levels (e.g., one is high and one is low). Phase difference 910 may be, for example, the product of the duty ratio of signal 908 and the mathematical constant pi.

An illustrative amplitude-cycle plot 914 (e.g., "Average Value of Vphi") is shown for the average value of signal 908 (e.g., "Vphi"). Cycles may be determined, for example, from a calculation of the ratio of durations 910 (e.g., "tau") and 912 (e.g., "T"). In the illustrative embodiment shown, the linear range of XOR logic gate 806 is pi radians.

Figure 10:
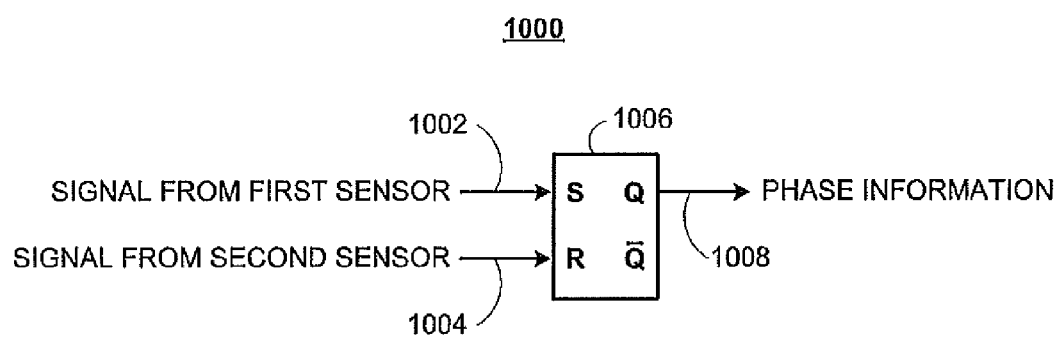
FIG. 10 is a block diagram of an illustrative flip-flop based phase detection system in accordance with an embodiment.

FIG. 10 is a block diagram of an illustrative flip-flop based phase detection system 1000 in accordance with some embodiments of the present disclosure. In some embodiments, phase detection system 1000 may be an illustrative implementation of phase detection system 322 (FIG. 3). For example, phase detection system 1000 may provide phase information to processor 312 to determine differential pulse transit time information, any other suitable information, or any combination thereof.

Phase detection system 1000 may include any suitable software, hardware, or both for determining phase information from two or more analog signals, such as signals 1002 (e.g., "signal from first sensor") and 1004 (e.g., "signal from second sensor"). For example, signals 1002 and 1004 may be generated by sensor unit 12 and sensor unit 13, respectively (FIG. 1), which may each include any of the physiological sensors described herein, or any other sensor. In another example, signals 1002 and 1004 may be generated from signal 316, which may be generated by pre-processor 320 coupled between processor 312 and sensor 318 (FIG. 3). In some embodiments, signals 1002 and 1004 may be generated from a multi-dimensional vector signal, a frequency- or time-multiplexed signal, any other suitable signal, or any combination thereof. For example, signals 1002 and 1004 may be PPG signals, which may be measured at two or more respective different body sites of a subject. In another example, signals 1002 and 1004 may be PPG signals filtered by a high pass filter, such as a derivative filter. In another example, signals 1002 and 1004 may be narrow pulses to avoid an overlap of "1" states at the inputs of flip-flop detector 1006.

Phase detection system 1000 may include any suitable components for performing phase measurements in the analog domain, such as flip-flop detector 1006, any other any other suitable component or circuitry, or any combination thereof. In some embodiments, flip-flop detector 1006 may process signals 1002 and 1004 to detect edges or transitions (e.g., the systolic pulse of a PPG signal) and output phase information via signal 1008. For example, flip-flop detector 1006 may analyze the difference in signals 1002 and 1004 and provide an output signal corresponding to the phase difference in the form of signal 1008.

Signal 1008 may be any suitable signal for providing phase information, such as an analog signal (e.g., voltage, current), digital signal, optical signal, multiplexed signal, multi-dimensional vector signal, any other suitable signal, or any combination thereof. For example, signal 1008 may be a voltage signal which represents the difference in phase between signals 1002 and 1004. In some embodiments, signal 1008 may be applied to a low-pass filter to provide an analog voltage proportional to the phase difference between signals 1002 and 1004.

Figure 11:
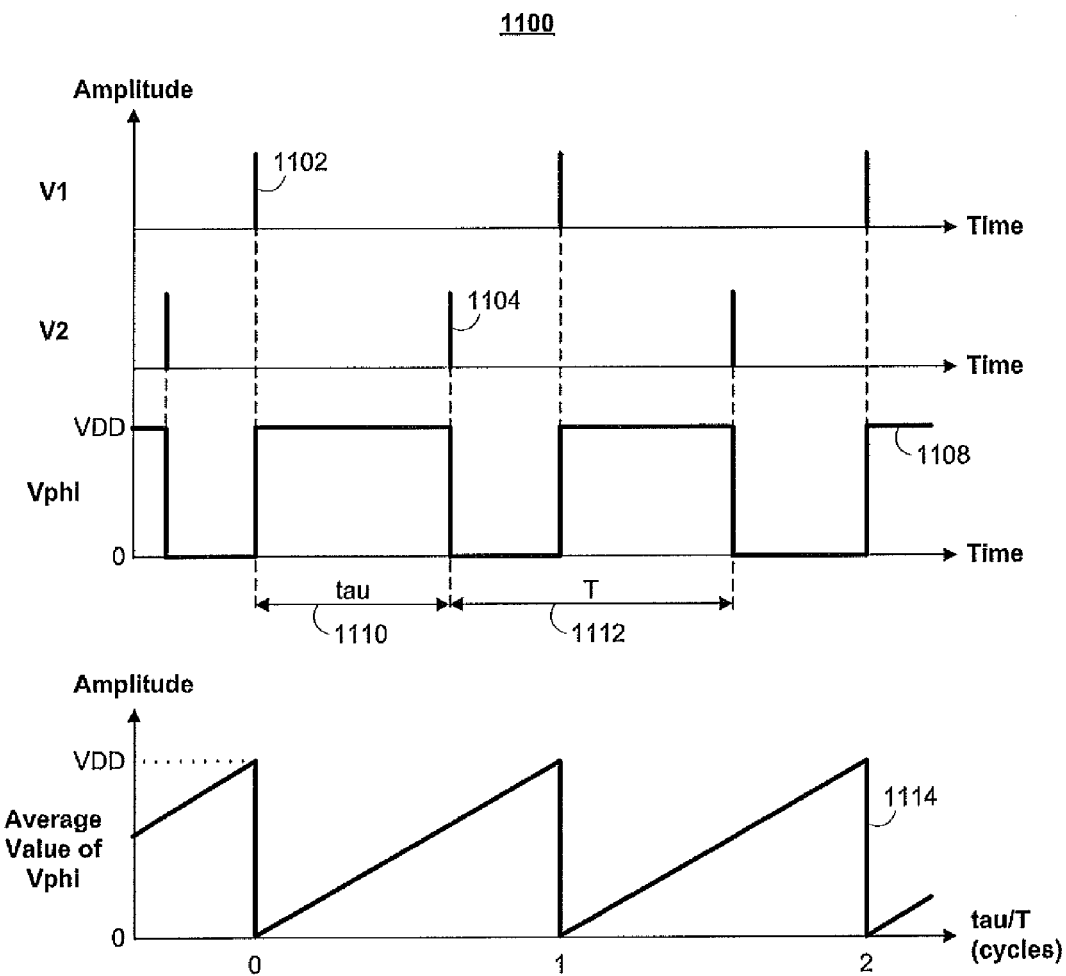
FIG. 11 shows illustrative signal plots for the phase detection system of FIG. 10 in accordance with an embodiment.

FIG. 11 shows illustrative amplitude-time signal plots 1100 for phase detection system 1000 (FIG. 10) in accordance with some embodiments of the present disclosure. Signal plots 1102, 1104, and 1108 are representative of signals 1002, 1004, and 1008, respectively. For example, phase detector 1006 may change state in response to, for example, a state change in signal 1102, 1104, or both. As an example, phase detector 1006 may change to the "Q=1" state (e.g., Vphi=VDD) with a "1" input from signal 1102 and to the "Q=0" state (e.g., Vphi=0) with a "1" input from signal 1104. The duration of the "Q=1" state (e.g., duration 1110) may depend on the time from the "1" input from signal 1102 to the "1" input from signal 1104. The duration of the "Q=1" state in signal 1108 (e.g., the average output voltage) may be proportional to the phase difference between signals 1102 and 1104.

An illustrative amplitude-cycle plot 1114 (e.g., "Average Value of Vphi") is shown for the average value of signal 1108 (e.g., "Vphi"). Cycles may be determined, for example, from a calculation of the ratio of durations 1110 (e.g., "tau") and 1112 (e.g., "T"). In the illustrative embodiment shown, the linear range of flip-flop detector 1006 is 2×pi radians.

Figure 12:
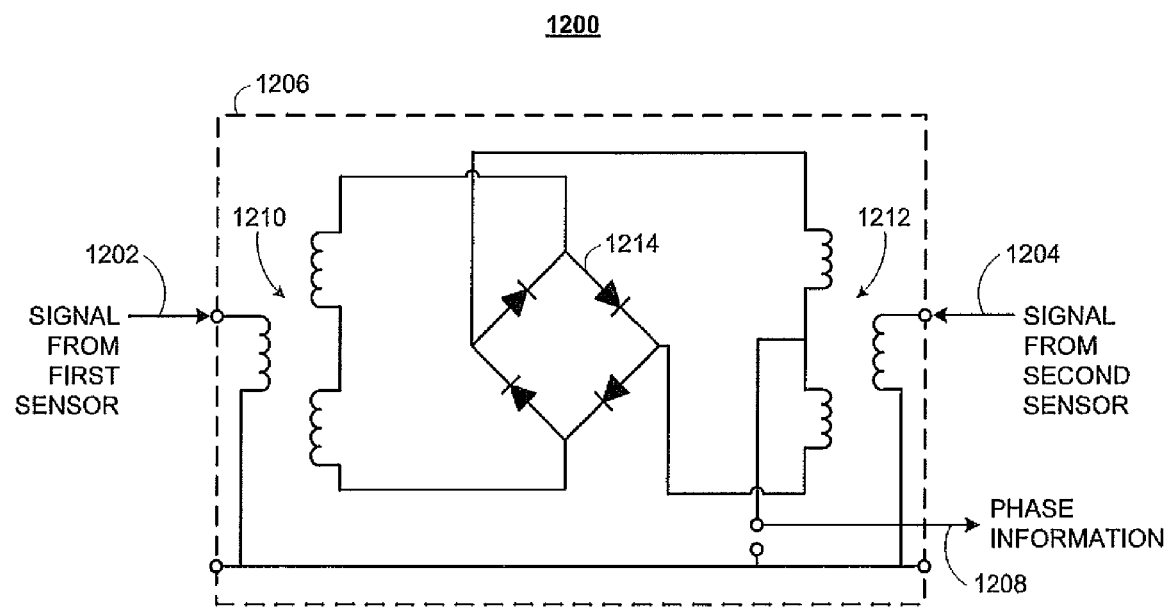
FIG. 12 is a block diagram of an illustrative mixer based phase detection system in accordance with an embodiment.

FIG. 12 is a block diagram of an illustrative mixer based phase detection system 1200 in accordance with some embodiments of the present disclosure. In some embodiments, phase detection system 1200 may be an illustrative implementation of phase detection system 322 (FIG. 3). For example, phase detection system 1200 may provide phase information to processor 312 to determine differential pulse transit time information, any other suitable information, or any combination thereof.

Phase detection system 1200 may include any suitable software, hardware, or both for determining phase information from two or more analog signals, such as signals 1202 (e.g., "signal from first sensor") and 1204 (e.g., "signal from second sensor"). For example, signals 1202 and 1204 may be generated by sensor unit 12 and sensor unit 13, respectively (FIG. 1), which may each include any of the physiological sensors described herein, or any other sensor. In another example, signals 1202 and 1204 may be generated from signal 316, which may be generated by pre-processor 320 coupled between processor 312 and sensor 318 (FIG. 3). In some embodiments, signals 1202 and 1204 may be generated from a multi-dimensional vector signal, a frequency- or time-multiplexed signal, any other suitable signal, or any combination thereof. For example, signals 1202 and 1204 may be PPG signals, which may be measured at two or more respective different body sites of a subject. In another example, signals 1202 and 1204 may be PPG signals convolved with a sinusoid to allow for ease of analysis by phase detection system 1200 because phase detection system 1200 may be, for example, more suited to receive a specific waveform such as a sinusoid.

Phase detection system 1200 may include any suitable components for performing phase measurements in the analog domain, such as double-balanced mixer 1206. Double-balanced mixer 1206 may include, for example, any suitable combination of diodes, inductors, transformers, resistors, wires, contact pads, input/output ports, any other suitable circuitry, or any combination thereof. For example, double-balanced mixer 1206 may be a Schottky diode-based double-balanced mixer and include, for example, unbalanced-to-balanced transformers 1210 and 1212 and diode ring 1214 (e.g., four Schottky barrier diodes). In seine embodiments, the ports for signals 1202, 1204, and 1208 may be accurately matched (e.g., terminated with an appropriate resistive load or source impedance) to allow for ease of measurement because of the termination impedance sensitivity of double-balanced mixer 1206.

In some embodiments, double-balanced mixer 1206 may process signals 1202 and 1204 and output phase information via signal 1208. For example, double-balanced mixer 1206 may multiply signals 1202 and 1204 together and provide an output signal corresponding to the mixer products (e.g., sum and difference frequencies) of signals 1202 and 1204 in the form of signal 1208 using a small angle approximation technique.

Signal 1208 may be any suitable signal for providing phase information, such as an analog signal (e.g., voltage, current), digital signal, optical signal, multiplexed signal, multi-dimensional vector signal, any other suitable signal, or any combination thereof. For example, signal 1208 may be a voltage signal which represents the difference in phase between signals 1202 and 1204.

Figure 13:
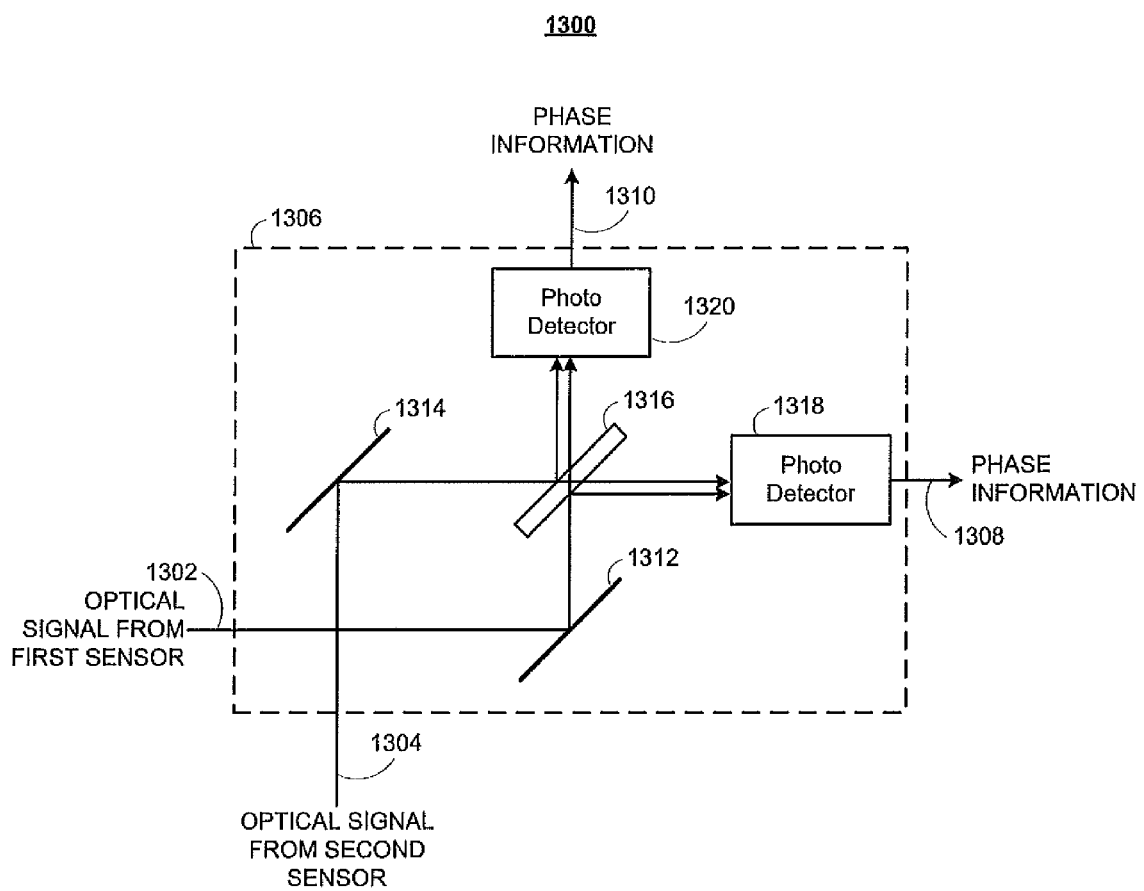
FIG. 13 is a block diagram of an illustrative optical phase detection system in accordance with an embodiment.

FIG. 13 is a block diagram of an illustrative optical phase detection system 1300 in accordance with some embodiments of the present disclosure. In some embodiments, optical phase detection system 1300 may be an illustrative implementation of phase detection system 322 (FIG. 3). For example, optical phase detection system 1300 may provide phase information to processor 312 to determine differential pulse transit time information, any other suitable information, or any combination thereof.

Optical phase detection system 1300 may include any suitable software, hardware, or both for determining phase information from two or more optical signals, such as optical oximetry sensor signals 1302 (e.g., "signal from first sensor") and 1304 (e.g., "signal from second sensor"). In some embodiments, optical oximetry sensor signals 1302 and 1304 may be generated by sensor unit 12 and sensor unit 13, respectively (FIG. 1), which may each include any of the physiological sensors described herein, or any other sensor. For example, optical oximetry sensor signals 1302 and 1304 may be generated from fiber optic channel 90 (FIG. 2). In some embodiments, optical oximetry sensor signals 1302 and 1304 may be generated from a multiplexed signal, any other suitable signal, or any combination thereof. For example, optical oximetry sensor signals 1302 and 1304 may be measured at two or more respective different body sites of a subject and may be multiplexed together to generate a single optical signal. Optical oximetry sensor signals 1302 and 1304 may be transmitted to optical phase detection system 1300 via any suitable communications path or paths, such as one or more fiber optic cables.

Phase detection system 1300 may include any suitable components for performing phase measurements in the optical domain, such as interferometer 1306, which may include one or more mirrors (e.g., mirrors 1312 and 1314), beam splitters (e.g., beam splitter 1316), detectors (e.g., photo detectors 1318 and 1320), fiberoptic cables, lenses, nonlinear crystals, wave plates, any other suitable components, or any combination thereof.

Interferometer 1306 may be implemented using any suitable configuration. In some embodiments, interferometer 1306 may be implemented as a Fabry-Perot interferometer, Michelson interferometer, Mach-Zehnder interferometer, any other suitable configuration, or any combination or permutation thereof. For example, interferometer 1306 may be implemented as a Mach-Zehnder style interferometer using a single beam splitter and a single transmission medium.

In some embodiments, interferometer 1306 may process optical oximetry sensor signals 1302 and 1304 and output phase information via signals 1308 and 1310. In an example, interferometer 1306 may receive optical oximetry sensor signals 1302 and 1304 as inputs. Optical oximetry sensor signals 1302 and 1304 may be transmitted to mirrors 1312 and 1314, respectively. Optical oximetry sensor signals 1302 and 1304 may then be transmitted to beam splitter 1316, which may be a polarizing beam splitter, a half-silvered mirror, a dichroic mirrored prism, any other suitable beam splitter, or any combination thereof.

Beam splitter 1316, may transmit, for example, half of the incident light from optical signal 1302 to photo detector 1320 and reflect, for example, half of the incident light from optical signal 1302 to photo detector 1318. Beam splitter 1316, may transmit, for example, half of the incident light from optical signal 1304 to photo detector 1318 and reflect, for example, half of the incident light from optical signal 1304 to photo detector 1320.

Photo detectors 1318 and 1320 may include any suitable software, hardware, or both for measuring interference patterns. Photo detectors 1318 and 1320 may include, for example, one or more CCD sensors, CMOS sensors, photodiodes, infrared (IR) sensors, ultraviolet sensors, temperature sensors, electronic processing equipment, any other suitable component, or any combination thereof. For example, photo detector 1318 may be a silicon photodiode based detector and photo detector 1320 may be an avalanche photodiode (APD) based detector. In another example, Photo detectors 1318 and 1320 may include features described in reference to detector 18 (FIG. 2).

In some embodiments, photo detectors 1318 and 1320 may include or be coupled to electronic processing equipment capable of determining phase information from the interference patterns of received optical signals. For example, photo detectors 1318 and 1320 may provide phase information in the form of signals 1308 and 1310, respectively. Signals 1308 and 1310 may be any suitable signals for providing phase information, such as analog signals (e.g., voltage, current), digital signals, optical signals, multiplexed signals, multi-dimensional vector signals, any other suitable signals, or any combination thereof. For example, signals 1308 and 1310 may be voltage signals which represent the difference in phase between signals 1302 and 1304 as measured by photo detectors 1318 and 1320, respectively. In some embodiments, signals 1308, 1310, or both may be used to determine, for example, differential pulse transit time.

Figure 14:
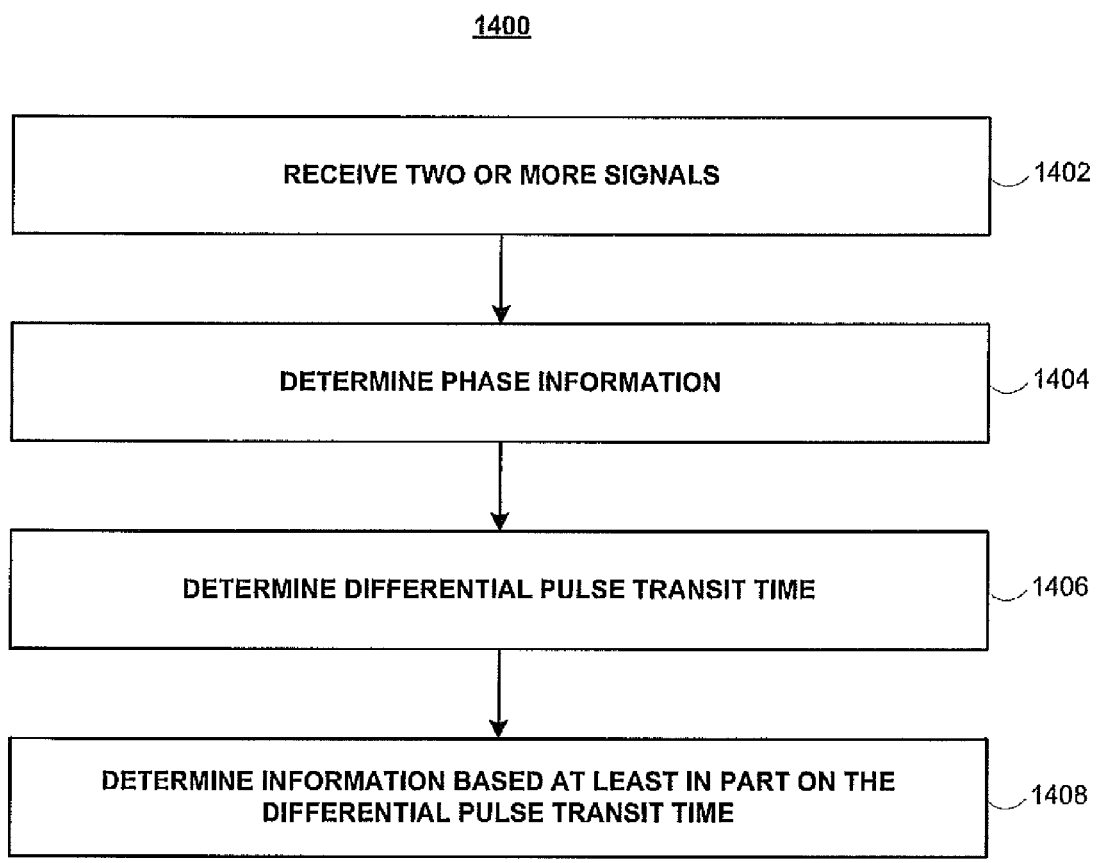
FIG. 14 is a flow chart am illustrative process for determining physiological information in accordance with an embodiment.

FIG. 14 is a flow diagram 1400 of illustrative steps involved in determining information from monitored signals in accordance with an embodiment. The steps of flow diagram 1400 may be performed by processor 312, phase detection system 322 (FIG. 3), or both, or may be performed by any suitable processing device communicatively coupled to monitor 14 (FIGS. 1 and 2). The steps of flow diagram 1400 may be performed by a digital processing device, implemented in analog hardware, or both. In an embodiment, the steps of flow diagram 1400 may be performed by a continuous, non-invasive blood pressure (CNIBP) monitoring system. It will be noted that the steps of flow diagram 1400 may be performed in any suitable order, and one or more steps may be omitted entirely according to the context and application.

At step 1402, two or more signals may be received. A signal (e.g., a PPG signal) may be received from any suitable source (e.g., patient 40 of FIG. 2) using any suitable technique. A received signal may be generated by sensor unit 12, sensor unit 13, or both (FIG. 1), which may each include any of the physiological sensors described herein, or any other sensor. A received signal may be signal 316, which may be generated by pre-processor 320 coupled between processor 312 and sensor 318 (FIG. 3). A received signal may include multiple signals, for example, in the form of a multi-dimensional vector signal or a frequency- or time-multiplexed signal. In an embodiment, the two or more signals received at step 1402 may include two or more PPG signals, which may be measured at two or more respective different body sites of a subject.

The two or more signals received at step 1402 may include first and second physiological signals received as input signal 316 (FIG. 3). In an embodiment, a first signal may be a Red PPG signal, and a second signal may be an IR PPG signal. In an embodiment, first and second signals may be different types of signals (e.g., a PPG signal and an ECG signal). In an embodiment, first and second signals may be obtained by first and second sensors located at approximately the same body site of a subject. In an embodiment, first and second signals may be obtained by first and second sensors located at different body sites of a subject. For example, first and second signals included in the two or more signals may be electronic signals, optical signals, or both from pulse oximetry sensors located at two different body sites of a subject.

In an embodiment, more than two signals may be received at step 1402. For example, PPG signals at three or more frequencies may be obtained at step 1402, or PPG signals from three or more body sites, or any set of three or more signals (such as two PPG signals and an ECG signal). It will be noted that the steps of flow diagram 1400 may be applied to any number of received signals in accordance with the techniques described herein.

At step 1404, phase information may be determined from the two or more signals received at step 1402. Step 1404 may occur in conjunction with the receiving at step 1402, or after the signals are received at step 1402. In some embodiments, the two or more signals may be input signals to a phase detection system, such as phase detection system 322 (FIG. 3), 600 (FIG. 6), 800 (FIG. 8), 900 (FIG. 9), 1200 (FIG. 12), 1300 (FIG. 13), any other suitable device, or any combination thereof. Phase information may be determined in any suitable manner in accordance with some embodiments of the present disclosure.

Processor 312, phase detection system 322 (FIG. 3), or both may transform the original signals, transformed signals, or both into any suitable domain. In an embodiment, the processing at step 1404 may include transforming a signal into another domain, such as a Fourier, wavelet, spectral, scale, time, time-spectral, time-scale domain, or any transform space using, for example, Processor 312. A transformation may include a continuous wavelet transformation as described, for example, in Paul S. Addison, The Illustrated Wavelet Transform Handbook (Taylor & Francis Group 2002), which is hereby incorporated by reference herein in its entirety.

In some embodiments, step 1404 may include filtering a signal 316 (FIG. 3), mathematically manipulating a signal, convolving a signal with a reference signal, any other suitable operation, or any combination thereof. For example, two signals may each be convolved with a square wave and provided as inputs to phase detection system 800 (FIG. 8).

Any of the operations described herein may be applied to a portion or portions of a received signal. An operation may be broken into one or more stages, performed by one or more devices, or both within signal processing system 300 of FIG. 3 (which may itself be a part of patient monitoring system 10 of FIGS. 1 and 2). For example, a filtering technique may be applied by input signal generator 310 (FIG. 3) prior to passing the resulting input signal 316 (FIG. 3) to processor 312, phase detection system 322 (FIG. 3), or both, where it may undergo a transformation, a calculation of phase information, or both. Embodiments of the steps of flow diagram 1400 include any of the operations described herein performed in any suitable order.

At step 1406, differential pulse transit time (DPTT) may be calculated based at least in part on the phase information determined at step 1404 and the two or more signals received at step 1402. For example, DPTT may be calculated using phase information provided in the form of signals 618 (FIG. 6), 808 (FIG. 8), 914 (FIG. 9), 1008 (FIG. 10), 1114 (FIG. 11), 1208 (FIG. 12), 1308, 1310 (FIG. 13), any other suitable phase information including processed information, or any combination thereof. The DPTT determined at step 1406 may be determined based at least in part on processing and comparison of any number of physiological signals (e.g., multiple PPG signals), including signals in which repeating features may be identified and processed either intra- or inter-pulse-wise.

In an embodiment, a weighted differential pulse transit time ($DPTT_{avg}$) may be calculated at step 1406 based at least in part on a linear combination of multiple fiducial points (e.g., peaks, valleys, any other suitable point, or any combination thereof) identified in the determination of the phase information. For example, a weighted differential pulse transit time ($DPTT_{avg}$) may be calculated from one or more processed signals in accordance with:

$$DPTT_{avg} = x DPTT_{first} + y DPTT_{second} + (1-x-y) DPTT_{pleth} \quad (19)$$

where $DPTT_{first}$ is a DPTT calculated between fiducial points identified in a first derivative of one or more received signals, $DPTT_{second}$ is a DPTT calculated between fiducial points identified in a second derivative of one or more received signals, $DPTT_{pleth}$ is a DPTT calculated between fiducial points identified in a PPG signal which has not been differentiated (but which may have been filtered or otherwise processed), and x and y are non-negative weights whose sum is less than or equal to 1. Multiple different weighted DPTTs may be calculated and used to determine multiple different types of physiological information. For example, one weighted DPTT may be used to calculate a patient's systolic blood pressure, while another weighted DPTT may be used to calculate a patient's diastolic blood pressure. In some embodiments, different fiducials within a same set of processed signals may be used (e.g., a combination of peaks, valleys, maximum and minimum slopes identified in a first or second derivative of the signals). For example, DPTTs may be calculated from the times of the maximum peak and minimum trough of the second derivative of a pulse's upstroke, then combined via a weighted combination to provide a measurement useful in calculating mean arterial pressure (MAP).

At step 1408, information about the subject based at least in part on the DPTT may be determined. In an embodiment, information determined at step 1408 may be physiological information. For example, physiological information determined at step 1408 may include a blood pressure of a subject (e.g., one or more of systolic and diastolic blood pressure). Some techniques that may be used to determine blood pressure based at least in part on parameters calculated from physiological signals are discussed above with reference to Eqs. 14-18. Other calculated parameters which benefit from this approach include: respiratory effort monitoring (in which changes in fiducial positioning may indicate localized changes in thoracic pressure), cardiac output monitoring (in which improvements in PPG fiducial placement and processing may benefit contour analysis techniques) and autonomic response measurements (in which heart rate variability techniques sometimes require the continuous and accurate reporting of the current pulse period).

In an embodiment, physiological information may be determined based at least in part on empirically-derived relationships between various parameters and the physiological information. For example, a parameter (e.g., an amplitude of a peak of a first derivative of a PPG signal) may be approximated by a first weighted combination of systolic blood pressure and diastolic blood pressure. Similarly, a parameter (e.g., an amplitude of a peak of a second derivative of a PPG signal) may be approximated by a second weighted combination of systolic blood pressure and diastolic blood pressure (different from the first weighted combination). Given the parameters, the systolic and diastolic blood pressures may be determined using these relationships.

After information about the subject is determined at step 1408, the information determined may be output to an output device. Information may be output through a graphical representation, quantitative representation, qualitative representation, or combination of representations via output 314 (FIG. 3) and may be controlled by processor 312 (FIG. 3). In an embodiment, output 314 (FIG. 4) may transmit physiological information by any means and through any format useful for informing a patient, a care provider, or a third party, of a patient's status and may involve recording the physiological information to a storage medium. Quantitative information, qualitative information, or both provided by output 314 (FIG. 3) may be displayed on a display (e.g., display 28 of FIG. 1). A graphical representation may be displayed in one, two, or more dimensions and may be fixed or change with time. A graphical representation may be further enhanced by changes in color, pattern, or any other visual representation. Output 314 (FIG. 3) may communicate the information by performing at least one of the following: presenting a screen on a display; presenting a message on a display; producing a tone or sound; changing a color of a display or a light source; producing a vibration; and sending an electronic message. Output 314 (FIG. 3) may perform any of these actions in a device close to a patient, or at a mobile or remote monitoring device as described previously. In an embodiment, output 314 (FIG. 3) may produce a continuous tone or beeping whose frequency changes in response to changes in a process of interest, such as a physiological process. In an embodiment, output 314 (FIG. 3) may produce a colored or flashing light that changes in response to changes in a physiological process of interest.

After or during the information determination of step 1408, the steps of flow diagram 1400 may be repeated. New signals may be received, or the information determination may continue on another portion of one or more of the previously received signals. In an embodiment, processor 312 (FIG. 3) may continuously or periodically perform steps 1402-1408 and update the information (e.g., as the patient's condition changes). The process may repeat indefinitely, until there is a command to stop the monitoring, until some detected event occurs that is designated to halt the monitoring process, or both. For example, it may be desirable to halt a monitoring process when a detected noise has become too great, a measurement quality has become too low, or, in a patient monitoring setting, when a patient has undergone a change in condition that can no longer be sufficiently well-monitored in a current monitoring configuration. In an embodiment, processor 312 (FIG. 3) may perform the steps of flow diagram 1400 at a prompt from a care provider via user inputs 56 (FIG. 2). In an embodiment, processor 312 (FIG. 3) may perform the steps of flow diagram 1400 at intervals that change according to patient status. For example, the steps of flow diagram 1400 may be performed more often when a patient is undergoing rapid changes in physiological condition, and performed less often as the patient's condition stabilizes.

The steps of flow diagram 1400 may be executed over a sliding window of a signal. For example, the steps of flow diagram 1400 may involve analyzing the previous N samples of the signal, or the samples of the signal received in the previous T units of time. The length of the sliding window over which the steps of flow diagram 1400 is executed may be fixed or dynamic. In an embodiment, the length of the sliding window may be based at least in part on the noise content of a signal. For example, the length of the sliding window may increase with decreasing measurement quality, increasing noise, or both, as may be determined by a measurement quality assessment, a noise assessment, or both. A subject's blood pressure may be monitored continuously using a moving PPG signal. PPG signal detection means may include a pulse oximeter and associated hardware, software, or both. A processor may continuously analyze the signal from the PPG signal detection means in order to continuously monitor a subject's blood pressure.

Any number of computational techniques, optimization techniques, or both may be performed in conjunction with the techniques described herein. For example, any known information regarding the physiological status of the patient may be stored in memory (e.g., ROM 52 or RAM 54 of FIG. 2). Such known information may be keyed to the characteristics of the patient, which may be input via user inputs 56 (FIG. 2) and used by monitor 14 (FIG. 2) to, for example, query a lookup table and retrieve the appropriate information. Additionally, any of the calculations and computations described herein may be optimized for a particular hardware implementation, which may involve implementing any one or more of a pipelining protocol, a distributed algorithm, a memory management algorithm, or any suitable optimization technique.

It will be understood that the foregoing is only illustrative of the principles of the disclosure, and that the disclosure may be practiced by other than the described embodiments, which are presented for purposes of illustration and not of limitation.

What is claimed is:

1. A method for determining physiological information about a subject, the method comprising:
   receiving two or more analog physiological signals of a subject;
   processing the analog physiological signals with a phase detector to generate phase information;
   determining using processing equipment two or more phase difference measurements indicative of differential pulse transit time based at least in part on the phase information; and
   determining using processing equipment physiological information about the subject based at least in part on the on a linear combination of the two or more phase difference measurements, wherein the physiological information comprises a blood pressure value.

2. The method of claim 1, wherein each of the two or more analog physiological signals comprise a photoplethysmograph signal.

3. The method of claim 2, wherein the two or more analog physiological signals are measured at two different sites of the subject.

4. The method of claim 1, wherein the phase detector is a logarithmic amplifier based phase detector.

5. The method of claim 1, wherein the two or more analog physiological signals comprise optical oximetry sensor signals measured at two different sites of the subject.

6. The method of claim 5, wherein the phase detector is an optical phase detector.

7. The method of claim 1, wherein each of the two or more phase difference measurements is based at least in part on one or more fiducial points of the two or more analog physiological signals.

8. The method of claim 7, wherein the two or more phase difference measurements are based at least in part on a linear combination of the fiducial points.

9. A system for determining physiological information about a subject, the system comprising:
   at least one signal input configured to receive two or more analog physiological signals of a subject;
   a phase detector coupled to the at least one signal input, the phase detector configured to process the analog physiological signals to generate phase information; and
   electronic processing equipment coupled to the at least one signal input and the phase detector, the electronic processing equipment configured to:
      determine two or more phase difference measurements indicative of differential pulse transit time based at least in part on the phase information; and
      determine physiological information about the subject based at least in part on the on a linear combination of the two or more phase difference measurements, wherein the physiological information comprises a blood pressure value.

10. The system of claim 9, wherein each of the two or more analog physiological signals comprise a photoplethysmograph signal.

11. The system of claim 10, wherein the two or more analog physiological signals are measured at two different sites of the subject.

12. The system of claim 9, wherein the phase detector is a logarithmic amplifier based phase detector.

13. The system of claim 9, wherein the two or more analog physiological signals comprise optical oximetry sensor signals measured at two different sites of the subject.

14. The system of claim 13, wherein the phase detector is an optical phase detector.

15. The system of claim 9, wherein the two or more phase difference measurements are based at least in part on one or more fiducial points of the two or more analog physiological signals.

16. The system of claim 15, wherein the each of the two or more phase difference measurements is based at least in part on a linear combination of the fiducial points.

17. Computer-readable medium for use in determining physiological information about a subject, the computer-readable medium having computer program instructions recorded thereon for:
   receiving two or more analog physiological signals of a subject;
   processing the analog physiological signals with a phase detector to generate phase information;
   determining two or more phase difference measurements indicative of differential pulse transit time based at least in part on the phase information; and
   determining physiological information about the subject based at least in part on the on a linear combination of the two or more phase difference measurements, wherein the physiological information comprises a blood pressure value.

18. The computer-readable medium of claim 17, wherein the two or more analog physiological signals are measured at two different sites of the subject.

* * * * *